(12) United States Patent
Kim et al.

(10) Patent No.: US 11,156,604 B2
(45) Date of Patent: Oct. 26, 2021

(54) MULTILAYER NANOWIRE COMPLEX AND METHOD OF PREPARING THE SAME

(71) Applicants: KOREA UNIVERSITY RESEARCH AND BUSINESS FOUNDATION, Seoul (KR); SNU R&DB Foundation, Seoul (KR)

(72) Inventors: Young Keun Kim, Seoul (KR); Yoo Sang Jeon, Seoul (KR); Da-yeon Nam, Incheon (KR); Yu Jin Kim, Seongnam-si (KR); Hang-Rae Kim, Seoul (KR); Hyun Mu Shin, Seoul (KR)

(73) Assignees: Korea University Research and Business Foundation, Seoul (KR); SNU R&DB Foundation, Seoul (KR)

(*) Notice: Subject to any disclaimer, the term of this patent is extended or adjusted under 35 U.S.C. 154(b) by 98 days.

(21) Appl. No.: 16/394,370

(22) Filed: Apr. 25, 2019

(65) Prior Publication Data

US 2019/0339260 A1 Nov. 7, 2019

(30) Foreign Application Priority Data

May 4, 2018 (KR) .......................... 10-2018-0051740

(51) Int. Cl.
*B82Y 15/00* (2011.01)
*G01N 33/543* (2006.01)
(Continued)

(52) U.S. Cl.
CPC ..... *G01N 33/54306* (2013.01); *G01N 33/533* (2013.01); *B82Y 5/00* (2013.01);
(Continued)

(58) Field of Classification Search
CPC ........... G01N 33/54306; G01N 33/533; G01N 2333/57; G01N 33/54346; G01N 33/553;
(Continued)

(56) References Cited

U.S. PATENT DOCUMENTS

| 2005/0101020 | A1 | 5/2005 | Salem et al. |
| 2011/0236260 | A1 | 9/2011 | Kim et al. |
| 2014/0363833 | A1* | 12/2014 | Bhatia ............. G01N 33/54306 435/7.94 |

FOREIGN PATENT DOCUMENTS

| JP | H11-242029 A | 9/1999 |
| JP | 2000-512008 A | 9/2000 |

(Continued)

OTHER PUBLICATIONS

Japanese Office Action dated Apr. 7, 2020 in corresponding Japanese Patent Application No. 2019-082068 (2 pages in Japanese).

(Continued)

*Primary Examiner* — Tracy Vivlemore
*Assistant Examiner* — Nam P Nguyen
(74) *Attorney, Agent, or Firm* — NSIP Law

(57) ABSTRACT

A method of preparing an immunological substance detection nanowire complex includes preparing a multilayer nanowire in which a first metal and a second metal are alternately stacked, attaching a polymer, having a carboxyl group and an amine group at both ends of the polymer, to the second metal, attaching a first antibody, treated with a thiol's group, to the first metal of the multilayer nanowire, and attaching a second antibody to the second metal through the carboxyl group of the polymer. The second antibody includes a phosphor.

6 Claims, 15 Drawing Sheets

(51) Int. Cl.
*G01N 33/533* (2006.01)
*B82Y 5/00* (2011.01)
*B82Y 40/00* (2011.01)

(52) U.S. Cl.
CPC ............... *B82Y 15/00* (2013.01); *B82Y 40/00* (2013.01); *G01N 2333/57* (2013.01)

(58) Field of Classification Search
CPC ........... G01N 33/582; G01N 33/56966; G01N 2333/555; B82Y 5/00; B82Y 15/00; B82Y 40/00
See application file for complete search history.

(56) References Cited

FOREIGN PATENT DOCUMENTS

WO      WO 02/093140 A1    11/2002
WO      WO 2010/074083 A1    7/2010

OTHER PUBLICATIONS

Extended European Search Report dated Jul. 26, 2019 in counterpart European Patent Application No. 19170012.9 (7 pages in English).

\* cited by examiner

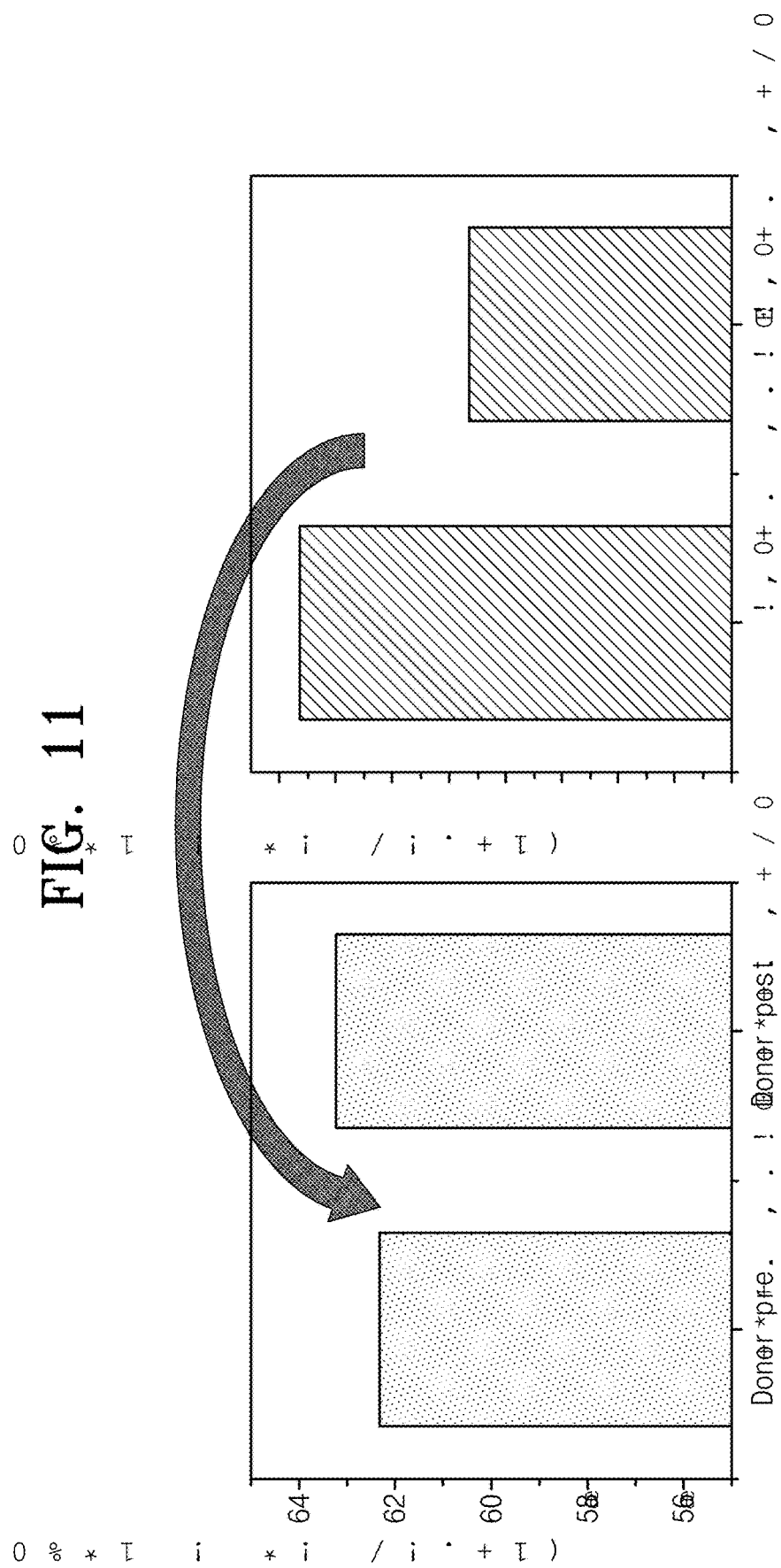

MULTILAYER NANOWIRE COMPLEX AND METHOD OF PREPARING THE SAME

CROSS-REFERENCE TO RELATED APPLICATIONS

This U.S. non-provisional patent application claims priority under 35 U.S.C. § 119 to Korean Patent Application No. 10-2018-0051740, filed on May 4, 2018, in the Korean Intellectual Property Office, the entire contents of which are hereby incorporated by reference.

TECHNICAL FIELD

The present disclosure relates to a fabrication method of a nanowire complex for detecting cells and biomolecules using a multilayer nanowire in which a first metal and a second metal are alternately stacked. More particularly, the present disclosure relates to a fabrication method of an immunological substance detection nanowire complex in which an antibody for capturing a cell and an antibody for detecting a biomolecule are selectively and simultaneously loaded on the first metal and the second metal, respectively.

BACKGROUND

In-vitro diagnosis of immunological substances is an inspection of measuring the number of immune cells or immunological substances, indicating the immunity of the human body, and quantitative analysis thereof has been used as an appropriate indicator for checking the immunity of an immune system. However, in the in-vitro diagnosis of immunological substances, separation of cells is required in respective processes such as capturing of immune cells, stimulation of immune cells, and detection of immunological substances (for example, cytokines). Each inspection process is complex, and problems of time and cost occur because different inspection apparatuses are required according to individual processes.

For example, a sandwich enzyme-linked immunosorbent assay (sandwich ELISA), an enzyme-linked immunospot assay (ELISPOT), flow cytometry, and the like have been used to detect a cytokine such as interferon-gamma (IFN-γ). These analysis methods indirectly detect cytokines distributed in blood, rather than directly detecting immune substances (for example, cytokines) released from immune cells. Accordingly, probability of error occurring in the inspection is high and a large amount of blood is required from a patient. Although the analysis method requires high cost and lots of time consumed, there is no substantially effective detection method to replace these analysis methods among existing technologies.

To address the above issue, nanomaterials each having high detection sensitivity have been used in various viewpoints. A core having magnetic properties, a core-shell nanoparticle containing biocompatible materials accumulated in a shell, a quantum dot having autofluorescence, and the like have been applied as representative nanomaterials. However, in the case of a nanoparticle, only a single antibody may be conjugated to a surface. Moreover, when two or more types of antibody are conjugated, there is a problem in conjugation efficiency and antibody binding efficiency due to interference between the antibodies.

SUMMARY

Example Embodiments of the present disclosure provide a multilayer nanowire complex in which an antibody for detecting a biomolecule and an antibody for capturing a cell are loaded.

Example embodiments of the present disclosure provide a fabrication method of a multilayer nanowire complex in which an antibody for detecting a biomolecule and an antibody for capturing a cell are loaded.

Example embodiments of the present disclosure provide a method of simultaneously capturing immune cells and detecting biomolecules secreted from the immune cells using a multilayer nanowire complex in which an antibody for detecting a biomolecule and an antibody for capturing a cell are loaded.

An aspect of the present disclosure provides a fabrication method of an immunological substance detection nanowire complex. The fabrication method includes preparing a multilayer nanowire in which a first metal and a second metal are alternately stacked, attaching a polymer, having a carboxyl group and an amine group at both ends of the polymer, to the second metal, attaching a first antibody, treated with a thiol's group, to the first metal of the multilayer nanowire, and attaching a second antibody to the second metal through the carboxyl group of the polymer. The second antibody includes a phosphor.

In example embodiments, the first metal may be gold (Au), and the second metal may be a ferromagnetic material including at least one of iron (Fe), nickel (Ni), and cobalt (Co).

In example embodiments, a polymer, having both a carboxyl group and an amine group at both ends thereof, may be connected with an ethyl group or polyethylene glycol.

In example embodiments, the polymer, having both a carboxyl group and an amine group at both ends thereof, may be 11-aminoundecanoic acid.

In example embodiments, the treatment of the thiol's group may be performed using 2-Iminothiolane or N-succinimidyl-S-acetylthioacetate (SATA) reactable with the amine group of the polymer.

In example embodiments, the first antibody may react earlier than the second antibody.

In example embodiments, the second antibody may bind to the polymer after being mixed with EDC(1-ethyl-3-(-3-dimethylaminopropyl) carbodiimide hydrochloride) and sulfo NHS (sulfo-N-hydroxysulfosuccinimide).

In example embodiments, the first metal of the multilayer nanowire may have a thickness of 20 nanometers (nm) to 50 nm, and the second metal of the multilayer nanowire may have a thickness of 20 nm to 50 nm.

An aspect of the present disclosure provides an immunological substance detection nanowire complex. The immunological substance detection nanowire complex includes a multilayer nanowire in which a first metal and a second metal are alternately stacked, a polymer, attached to the second metal, having a carboxyl group and an amine group at both ends thereof, a first antibody attached to the first metal group of the multilayer nanowire after being treated with a thiol's group, and a second antibody attached to the second metal through the carboxyl group of the polymer. The second antibody includes a phosphor.

In example embodiments, the first antibody may sandwich-bind to an immunological substance and a first auxiliary antibody, the first auxiliary antibody may include an auxiliary phosphor, the second antibody may bind to an immune cell, a phosphor of the second antibody may receive external light to provide first fluorescence, and the auxiliary phosphor of the first antibody may receive the first fluorescence of the phosphor of the second antibody to provide second fluorescence.

In example embodiments, the first metal may be gold (Au), and the second metal may be a ferromagnetic material including at least one of iron (Fe), nickel (Ni), and cobalt (Co).

In example embodiments, a polymer, having both a carboxyl group and an amine group at both ends thereof, may be connected with an ethyl group or polyethylene glycol.

In example embodiments, a polymer, having both a carboxyl group and an amine group at both ends thereof, may be 11-aminoundecanoic acid.

In example embodiments, the first metal of the multilayer nanowire may have a thickness of 20 nanometers (nm) to 50 nm, and the second metal of the multilayer nanowire may have a thickness of 20 nm to 50 nm.

An aspect of the present disclosure provides a method of detecting an immunological substance. The method includes preparing a nanowire complex including a multilayer nanowire in which a first metal and a second metal are alternately stacked, a first antibody attached to the first metal, a polymer attached to the second metal, and a second antibody including a phosphor and attached to the polymer, preparing an immune cell solution containing an immune cell, mixing the nanowire complex with the immune cell solution to produce a first mixed solution and reacting the immune cell with the second antibody, introducing a first auxiliary antibody, containing an auxiliary phosphor, into the first mixed solution, in which the nanowire complex and the immune cell solution are mixed, to produce a second mixed solution and to sandwich-bind an immunological substance, the first antibody, and the first auxiliary antibody released by the immune cell, and irradiating excitation light to the second mixed solution in such a manner that the phosphor emits light and light emission of the auxiliary phosphor by the emission of the phosphor is detected.

In example embodiments, the method may further include removing the first auxiliary antibody which does not sandwich-binds to the first antibody.

In example embodiments, the method may further include removing a nanowire complex in which the immune cell does not react to the second antibody.

In example embodiments, the immune cell may be a CD8+ T-cell, and the immunological substance may be interferon-gamma (IFN-γ).

In example embodiments, the first metal may be gold (Au), and the second metal may be a ferromagnetic material including at least one of iron (Fe), nickel (Ni), and cobalt (Co).

In example embodiments, a polymer, having both a carboxyl group and an amine group at both ends thereof, may be connected with an ethyl group or polyethylene glycol.

BRIEF DESCRIPTION OF THE DRAWINGS

The present disclosure will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the present disclosure.

FIG. 11 illustrates a result obtained by confirming an increase in fluorescent intensity of a donor after bleaching fluorescence of an acceptor to check fluorescent resonance energy transfer (FRET) occurring between a phosphor and an auxiliary phosphor.

DETAILED DESCRIPTION

A multilayer nanowire includes biocompatible materials and has a structure in which two metals are alternately stacked. Although the multilayer nanowire is expected to have significantly high applicability, it is difficult to analyze a specimen by simultaneously conjugating two or more types of antibody. Accordingly, applicability of the multilayer nanowire is limited.

A nanowire complex according to an example embodiment of the present disclosure includes a multilayer nanowire in which a first metal and a second metal are alternately stacked. An antibody for detecting a biomolecule is conjugated to the first metal of the multilayer nanowire, and an antibody for capturing a cell is conjugated to the second metal of the multilayer nanowire. The antibody for capturing a cell includes a fluorescent substance and binds to an immune cell. An antibody for detecting a biomolecule, including an immunological substance and an externally injected auxiliary phosphor, performs sandwich binding. Externally provided light induces a light emission of a phosphor, and the emission of the phosphor causes the auxiliary phosphor to be emitted by fluorescence resonance energy transfer (FRET). That is, immunological substances may be detected using the fluorescence resonance energy transfer (FRET).

According to an example embodiment of the present disclosure, a nanowire, in which a first metal (Au) and a second metal (Fe) are alternately stacked, is prepared. A polymer, having both a carboxyl group and an amine group at both ends thereof, is attached to the second metal (Fe). A first antibody (an antibody for detecting a biomolecule) treated with a thiol's group is attached to the first metal (Au) of the nanowire. The second antibody (antibody for capturing an immune cell), including a phosphor, is attached to the second metal (Fe) through the carboxyl group of the polymer. Externally supplied excitation light indices a phosphor to emit a light. The emission of the phosphor induces a light emission of the auxiliary phosphor, included in the first antibody (antibody for detecting a biomolecule) sandwich-binding to the first antibody (antibody for detecting a biomolecule), by the fluorescence resonance energy transfer (FRET).

Hereinafter, the present disclosure will be described in more detail based on example embodiments. However, these embodiments are just for better understanding of the present disclosure, and it is obvious to those skilled in the art that the present disclosure is not limited or restricted by experiment conditions, materials, or the like of the example embodiments.

Figure 1:
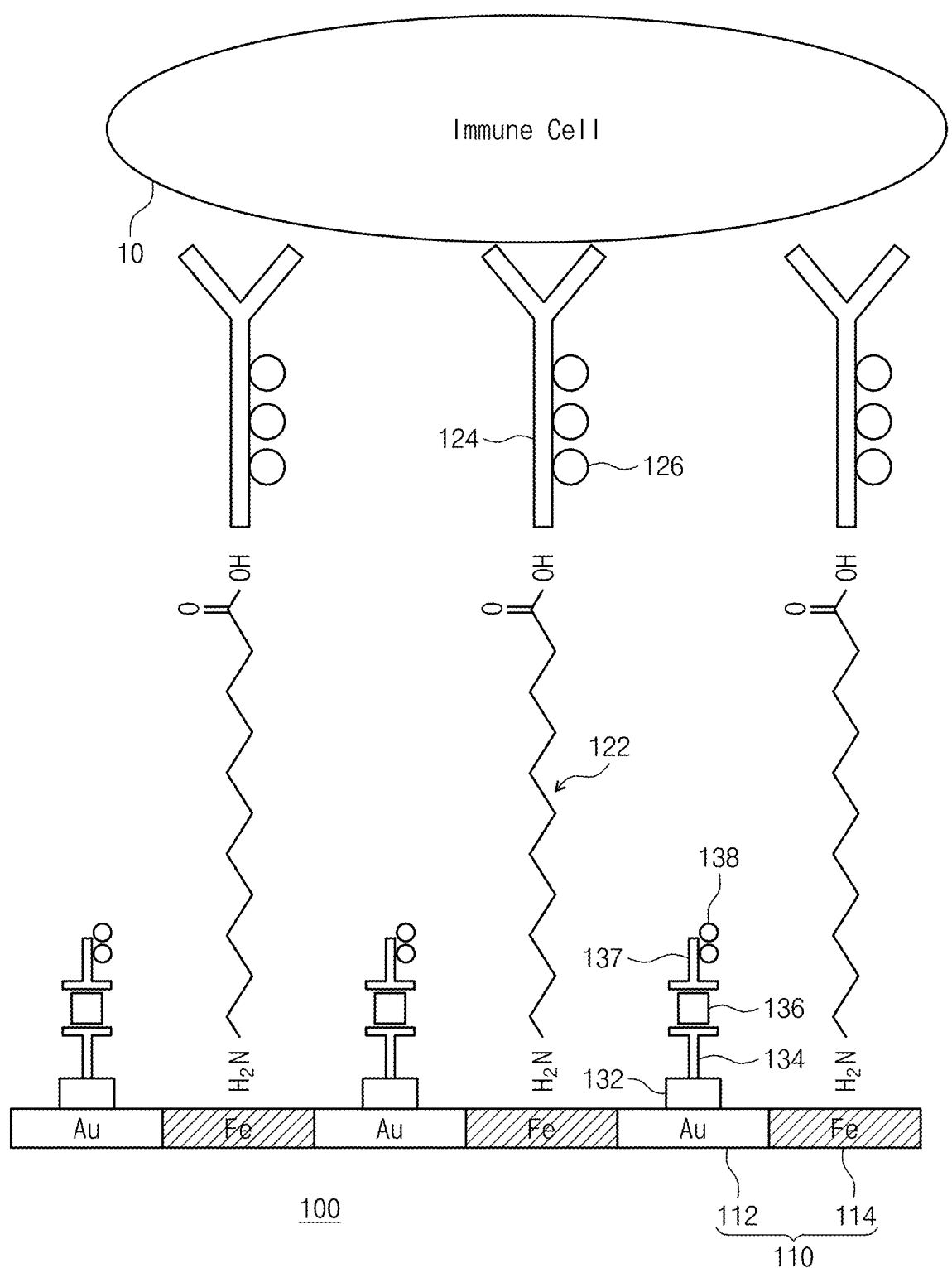
FIG. 1 is a concept diagram illustrating an immunological substance detection method according to an example embodiment of the present disclosure.

FIG. 1 is a concept diagram illustrating an immunological substance detection method according to an example embodiment of the present disclosure.

Referring to FIG. 1, an immunological substance detection nanowire complex 100 includes a multilayer nanowire 110 in which a first metal 112 and a second metal 114 are alternately stacked, a polymer 122 attached to the second metal 114 and having a carboxyl group and an amine group at both ends thereof, a first antibody 134 attached to the first metal 112 of the multilayer nanowire 110 after being treated with a thiol's group, and a second antibody 124 attached to the second metal 114 through the carboxyl group of the polymer 122. The second antibody 124 includes a phosphor 126. The first antibody 134 sandwich-binds to a first auxiliary antibody 137 including an immunological substance (interferon-gamma, IFN-γ) and an auxiliary phosphor 138. The second antibody 124 binds to an immune cell. The phosphor 126 of the second antibody 124 receives excitation light to provide first fluorescence, and the auxiliary phosphor 138 of the first auxiliary antibody 137 receives the fluorescence of the phosphor 126 of the second antibody 124 to provide second fluorescence. The first antibody 134 may be an antibody for detecting a biomolecule, and the second antibody may be an antibody for capturing an immune cell.

The second antibody 124 captures the immune cell (for example, CD8+ T cell). The immune cell 10 secrete an immunological substance 136 due to stimulation of the second antibody 124 or an antigen. The immunological substance 136 may be interferon-gamma (IFN-γ). The immunological substance 136 binds to the first antibody 134. The immunological substance 136 also performs sandwich-binding to the first auxiliary antibody 137, including the auxiliary phosphor 138, and the first antibody 134. The first auxiliary antibody 137 may be the same as the first antibody 134 except that the auxiliary phosphor 138 is attached and an antigen binding site is different. An excitation light source causes the phosphor 126 of the second antibody 124 to emit light. When the phosphor 126 and the auxiliary phosphor 138 are near averagely within 10 nanometers, energy may be transferred by resonance. Accordingly, the auxiliary phosphor 138 may emit light. Energy is not transferred by resonance when the phosphor 126 and the auxiliary phosphor 138 are at a long distance of several hundred nanometers or more. The phosphor 126 is Brillant Violet™ BV421, and the auxiliary phosphor may be Alexa Fluor™ AF488.

The first metal 112 may be gold, and the second metal 114 may be a ferromagnetic material including at least one of iron (Fe), nickel (Ni), and cobalt (Co). The first metal 112 of the multilayer nanowire 110 may have a thickness of 20 nm to 50 nm, and the second metal 114 of the multilayer nanowire 110 may have a thickness of 20 nm to 50 nm.

The polymer may have a carboxyl group and an amine group at both ends thereof. The polymer may be connected with an ethyl group or polyethylene glycol. The polymer may be 11-aminoundecanoic acid.

Accordingly, the immunological substance detection nanowire complex 100 may selectively detect only the immunological substance 136, secreted from a specific immune cell, and may provide an amount of the immunological substance 136 as an intensity of the light emission of the auxiliary phosphor 138. This immunological substance detection method may detect a concentration of 724 pg/mL of the immunological substance (interferon-gamma) which cannot be detected by a conventional method.

FIGS. 2A to 2D illustrate a fabrication method of an immunological substance detection nanowire complex according to another example embodiment of the present disclosure.

A fabrication method of an immunological substance detection nanowire complex includes: preparing a multilayer nanowire 110 in which a first metal 112 and a second metal 114 are alternately stacked; attaching a polymer 122, having a carboxyl group and an amine group at both ends of the polymer 122, to the second metal 114; attaching a first antibody 134, treated with a thiol's group 132, to the first metal 112 of the multilayer nanowire 110; and attaching a second antibody 124, including s phosphor 126, to the second metal 114 through the carboxyl group of the polymer 122.

Synthesis of Multilayer Nanowire

Figure 2A:
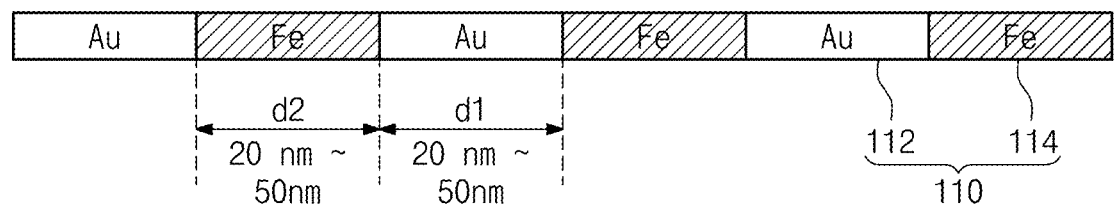
FIGS. 2A to 2D illustrate a method of preparing an immunological substance detection nanowire complex according to another example embodiment of the present disclosure.
Figure 2B:
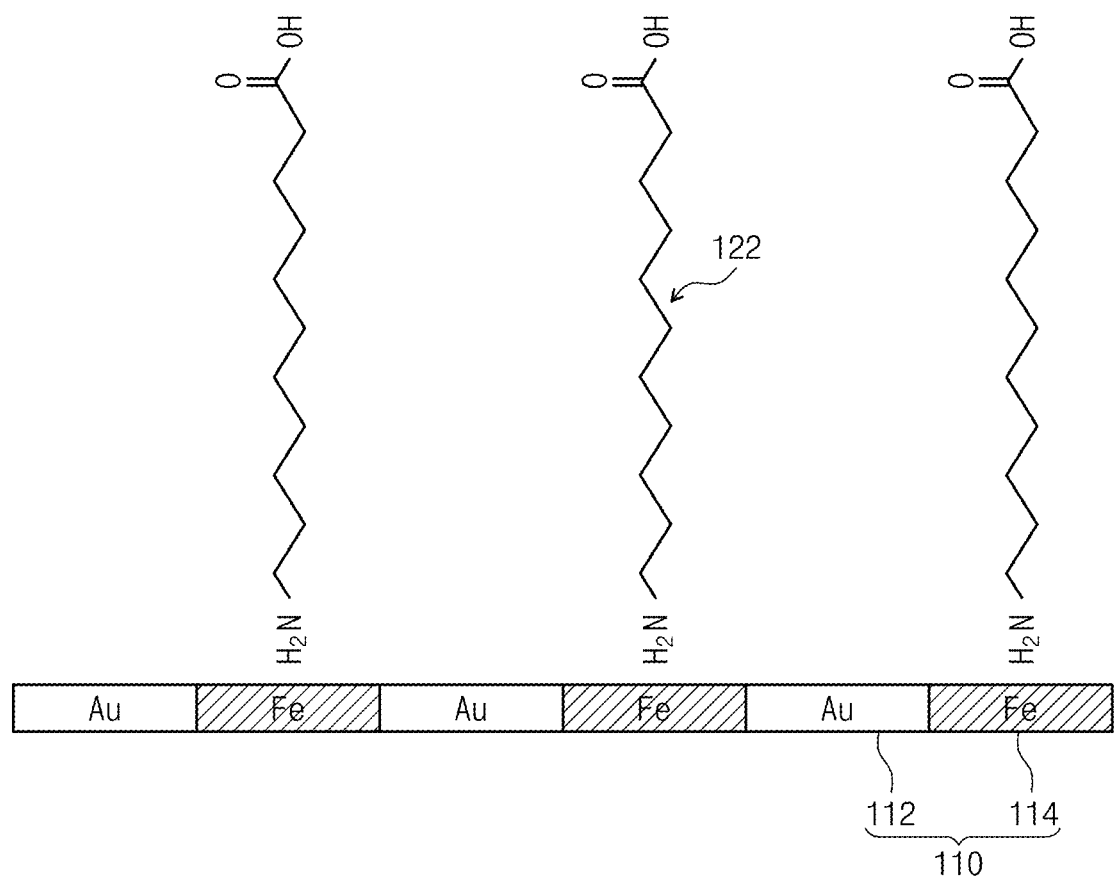
Figure 2C:
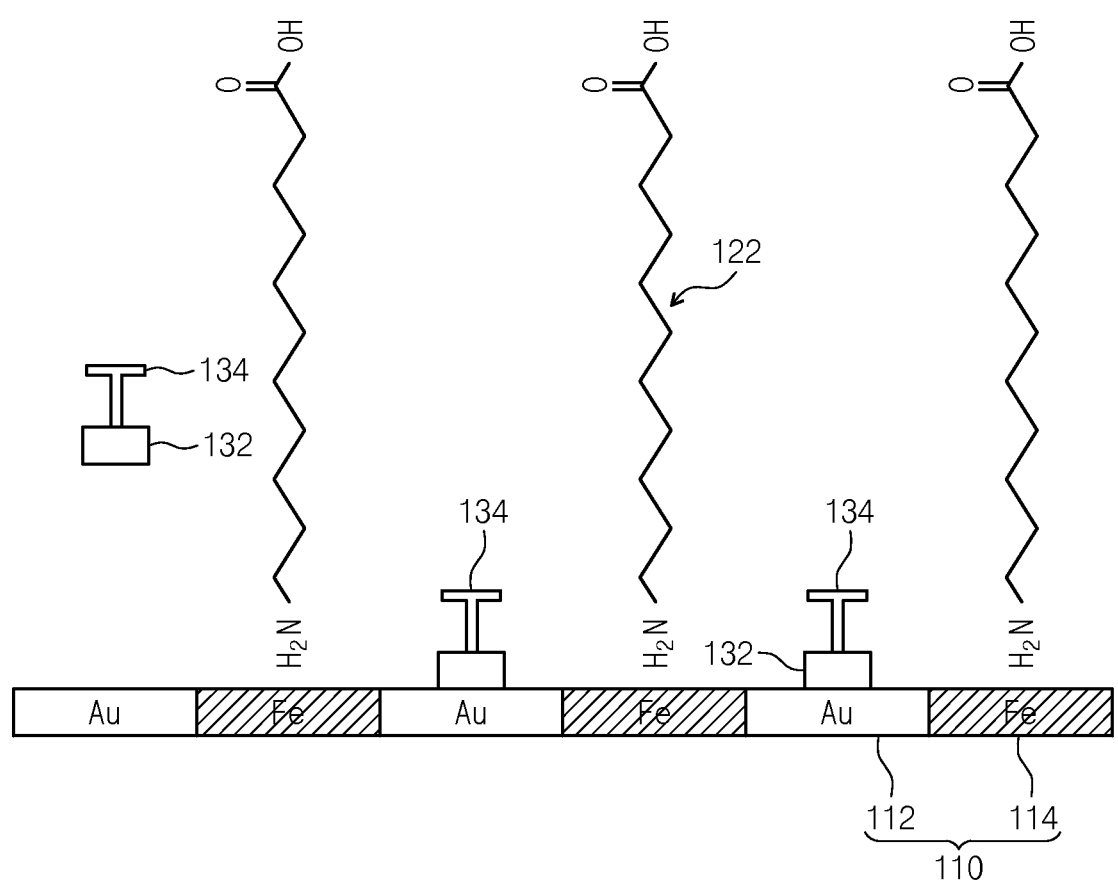
Figure 2D:
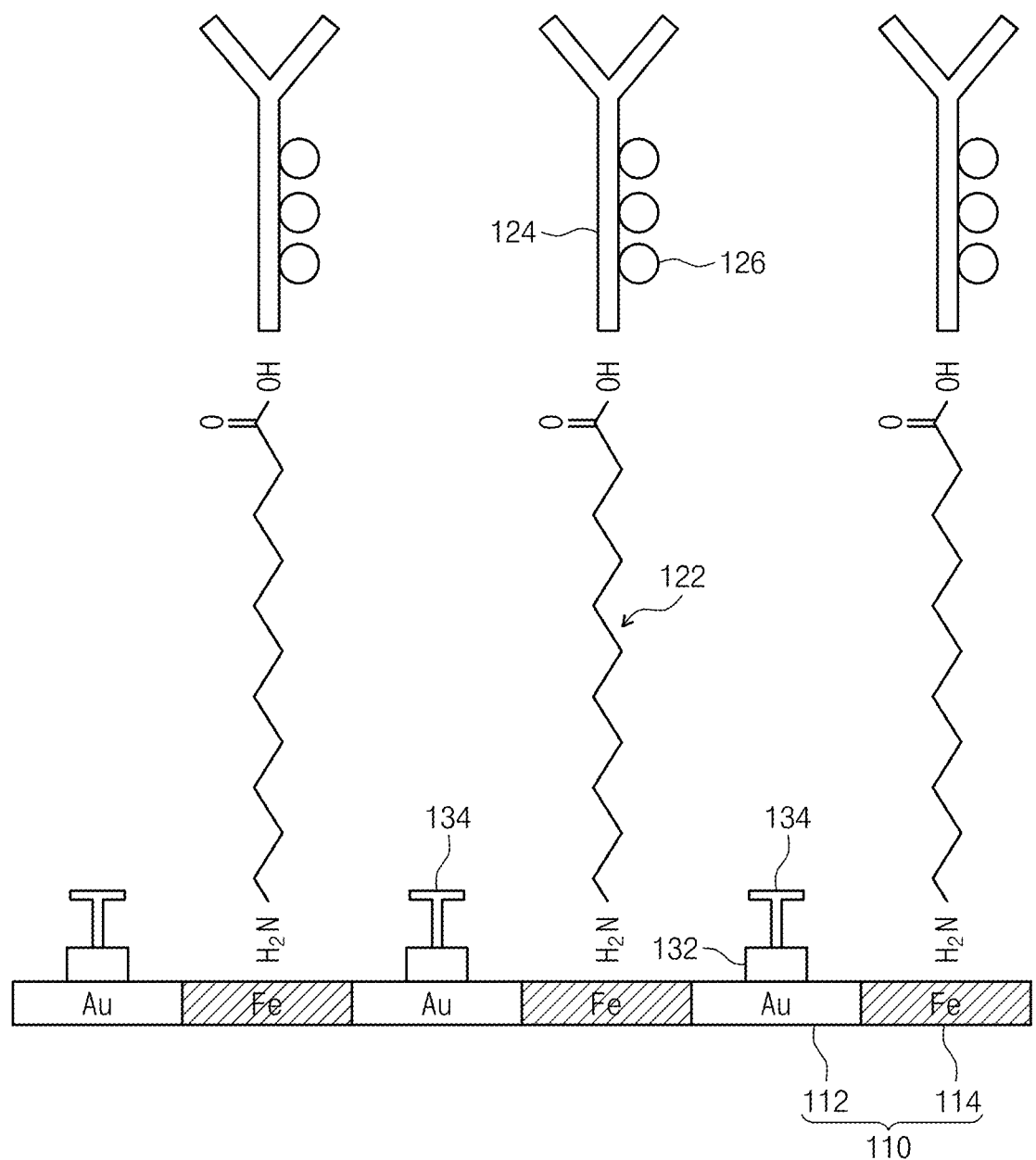

Referring to FIG. 2A, synthesis of a barcode-type iron/gold (Fe/Au) multilayer nanowire 110 is performed in a single plating bath by a pulsed electrodeposition method. A deionized water-based solution to be used in the plating bath includes precursor iron sulfate heptahydrate ($FeSO_4 \cdot 7H_2O$, 0.16 M), potassium dicyanoaurate (I), $K[Au(CN)_2]$, 0.01 M), and boric acid ($H_3BO_3$, 0.80 M) which is a buffer.

An anodized aluminum oxide (AAO) is used as a nanotemplate to be electroplated. The nanotemplate has a plurality of pores having a diameter of several hundred nanometers. By an e-beam evaporator, 300 nm of silver (Ag) is deposited on one surface of the nanotemplate. The deposited silver (Ag) may be used as a working electrode of electroplating, and a platinum (Pt) electrode plate is used as a counter electrode.

To reduce the first metal (gold) and the second metal (iron) in a single bath state, current densities of 10 $mA/cm^2$ and 1 $mA/cm^2$ were applied in the form of a pulse, respectively. The multilayer nanowire 110 is synthesized on the nanotemplate.

The working electrode may be removed with an iodine (I)-based silver corrosion solution. Then, anodized aluminum nanotemplate may be selectively removed with sodium hydroxide (NaOH, 1M). The second metal (iron) may have a thickness of 20 nm and 50 nm. The first metal (gold) may have a thickness of 20 nm and 50 nm.

The multilayer nanowire 110 inside the nanotemplate was obtained by washing the nanotemplate with deionized water five times or more using a centrifuge. A dispersed multilayer nanowire solution was substituted with phosphate buffered saline (PBS) for surface biofunctionalization.

Treatment and Characteristic Analysis of Multilayer Nanowire Surface Functional Group A surface treatment of the multilayer nanowire 110 is performed by adding 11-aminoundecanoic acid, having both an amine group and a carboxyl group at both ends thereof, to a second metal (iron). The 11-aminoundecanoic acid may have an amine group and a carboxyl group at both ends thereof. Specifically, the 11-aminoundecanoic acid is dissolved in phosphorylation buffered solution at 6 mM. The multilayer nanowire 110 dispersed in 1 mL of phosphorylation buffered solution and 1 mL of an aminoundecanoic acid solution are mixed at a ratio of 1:1. The mixed solution is shaken using a shaker at room temperature for 8 hours or more. The amine group of the 11-aminoundecanoic acid is attached to the surface of the second metal (iron). After a reaction is completed, residues are removed by a cleaning method using a centrifuge.

Antibody Complexation Method of First Metal (Gold) of Multilayer Nanowire

Two chemical reactions were used to conjugate two heterogeneous antibodies to different parts of the multilayer nanowire 110, respectively. A 2-iminothiolane solution (a traut's reagent) was prepared at a concentration of 2 mg/mL to conjugate the thiol's group on a surface of the antibody for immunological substance detection (the first antibody). Then, 50 μL is taken out of the solution and mixed with 50 μL of the antibody for immunological substance detection (the first antibody). After reacting at room temperature for 2 hours, the antibody is cleaned using spin desalting columns.

0.5 mL of a multilayer nanowire solution, sufficiently dispersed with an antibody for immunological substance detection (first antibody) treated with a thiol's group, and 0.5 mL of ethylenediaminetetraacetic acid (EDTA) reacted at room temperature for two hours to conjugate the antibody to the first metal (gold). The first metal 112 of the multi-layer nanowire 110 binds to the antibody for immunological substance detection (the first antibody) treated with the thiol's group. When the binding reaction between the antibody for immunological substance detection (the first antibody) and the first metal (gold) of the multilayer nanowire 110 is completed, the antibody is cleaned three times or more with a phosphorylation buffered solution.

Antibody Complexation Method of Second Metal (Iron) of Multilayer Nanowire

The antibody for capturing an immune cell (the second antibody) 124 is selectively conjugated to the second metal (iron). In this case, 30 μL of the antibody for capturing an immune cell 124, 0.4 mL of EDC (1-ethyl-3-(3-dimethylaminopropyl) carbodiimide hydrochloride), and 0.5 mL of sulfo-N-hydroxysulfosuccinimide are mixed with the multilayer nanowire solution and react at room temperature for two hours using a shaker. From the standpoint of the antibody for capturing an immune cell (the second antibody) subjected to the second conjugation process, steric hindrance may be caused by a process of reacting the antibody for immunological substance detection (the first antibody), to which the thiol's group is conjugated, with the first metal (gold). Accordingly, the steric hindrance may play a decisive role in selectively attaching the antibody for capturing an immune cell (the second antibody) to the second metal (iron). The antibody for capturing an immune cell (the second antibody) includes a phosphor 126. The phosphor may be BV421 (trade name).

Figure 3:
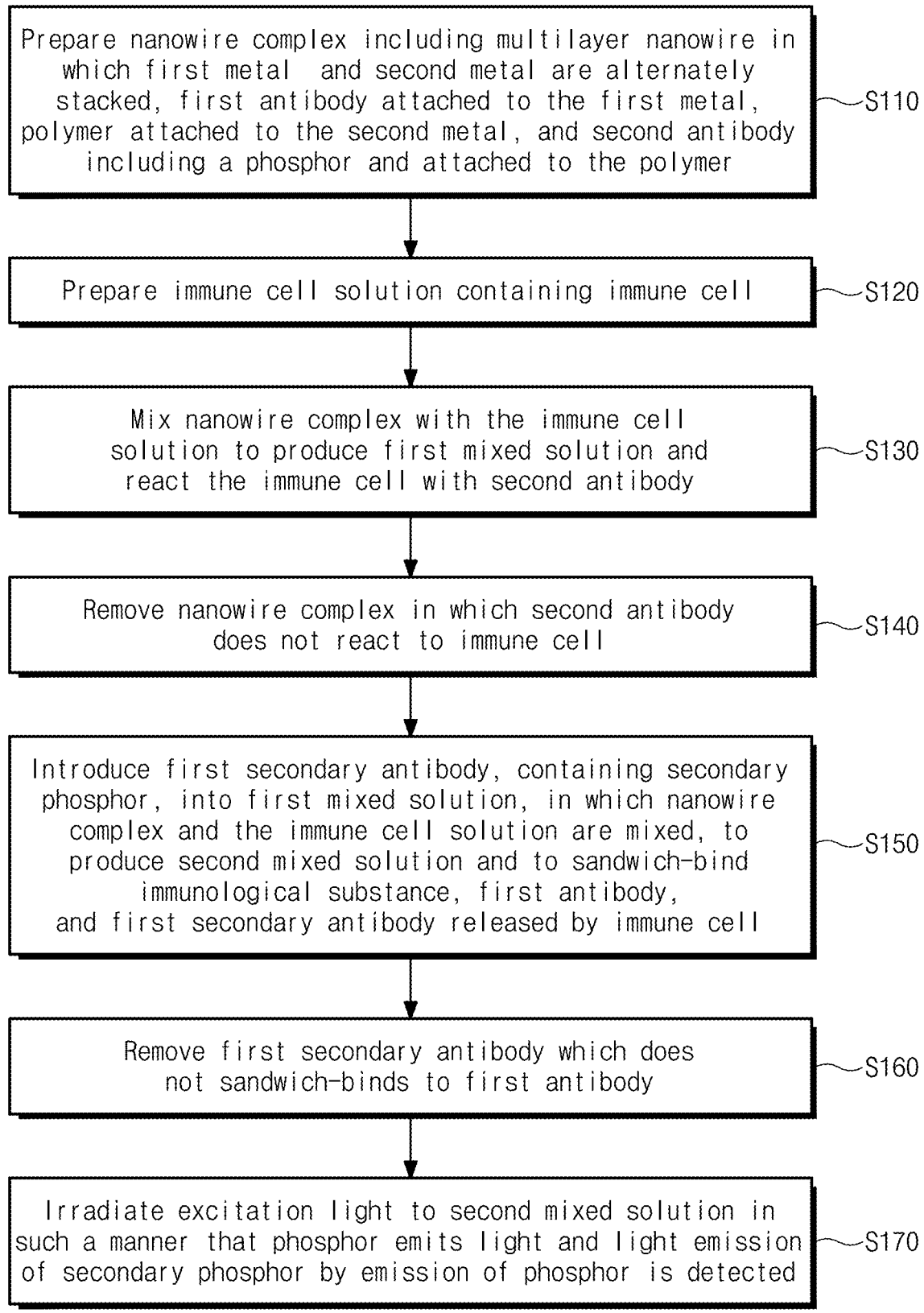
FIG. 3 is a flowchart illustrating a method of detecting an immunological substance according to an example embodiment of the present disclosure.

FIG. 3 is a flowchart illustrating a method of detecting an immunological substance according to an example embodiment of the present disclosure.

Figure 4A:
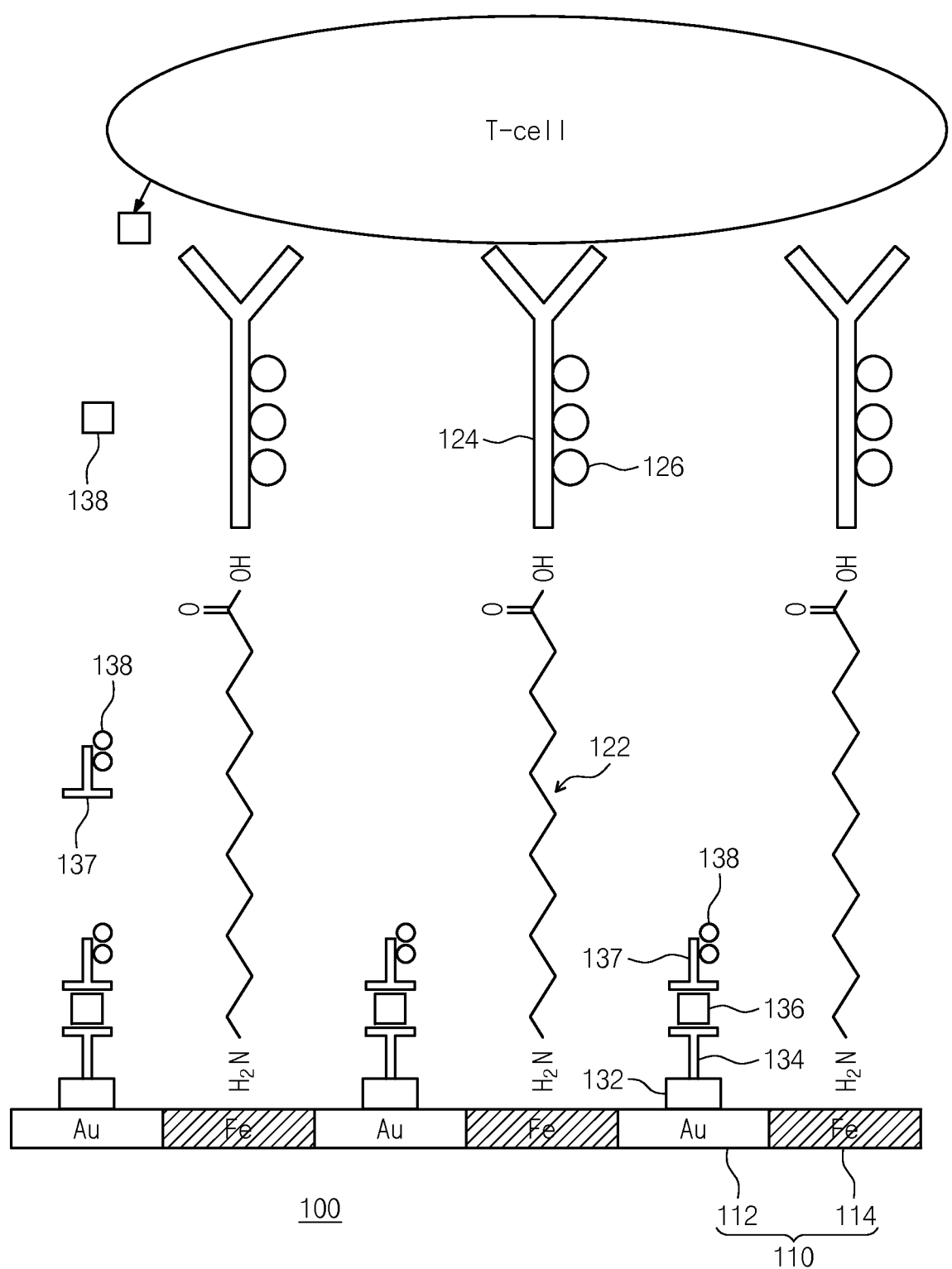
FIGS. 4A and 4B are concept diagrams illustrating a method of detecting an immunological substance according to an example embodiment of the present disclosure.
Figure 4B:
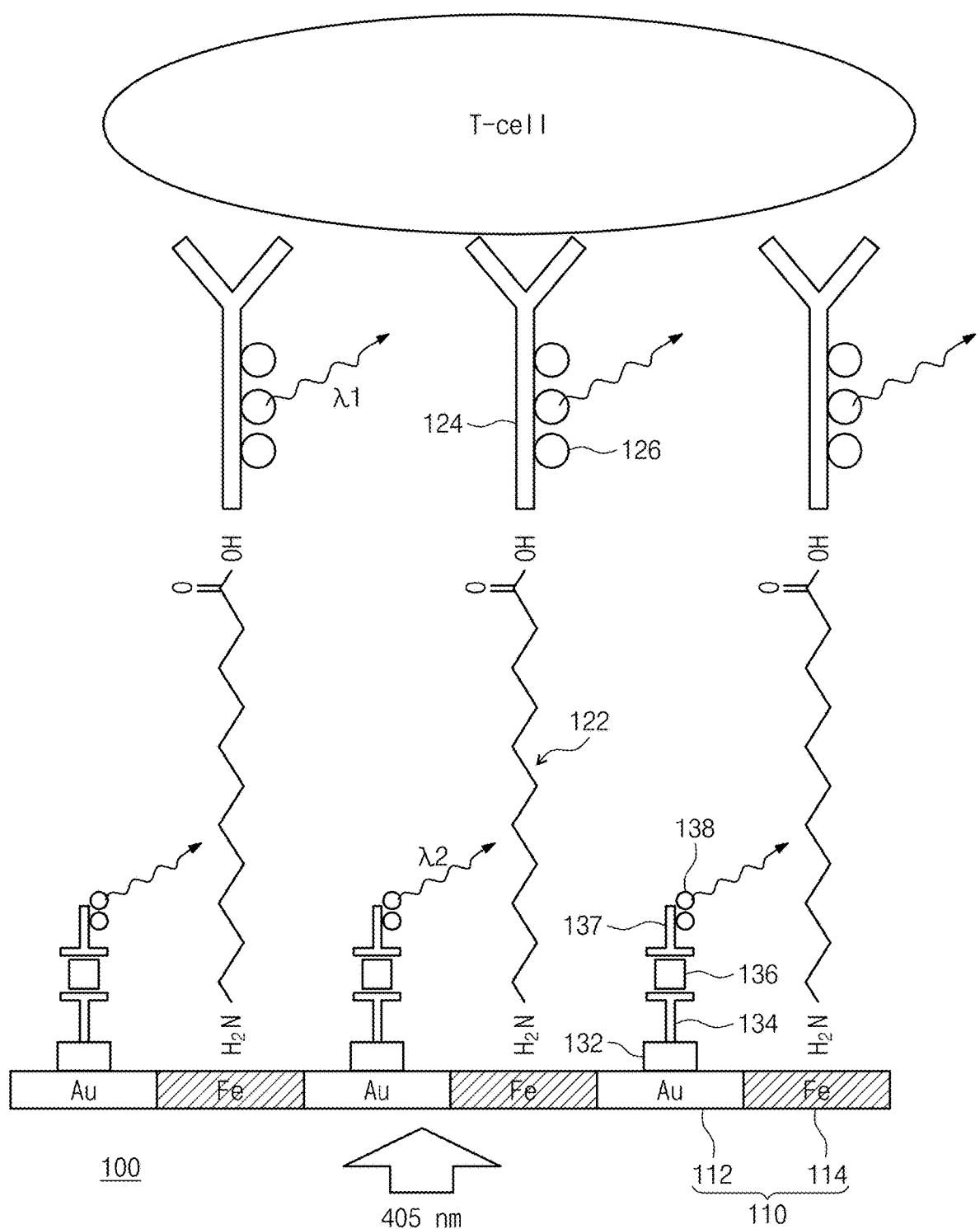

FIGS. 4A and 4B are concept diagrams illustrating a method of detecting an immunological substance according to an example embodiment of the present disclosure.

Referring to FIGS. 3, 4A, and 4B, a method of detecting an immunological substance according to an example embodiment of the present disclosure includes: preparing a nanowire complex 100 including a multilayer nanowire in which a first metal 112 and a second metal 112 are alternately stacked, a first antibody 134 attached to the first metal 112, a polymer attached to the second metal 112, and a second antibody 124 including a phosphor and attached to the polymer (S110); preparing an immune cell solution containing an immune cell 10 (S120); mixing the nanowire complex 100 with the immune cell solution to produce a first mixed solution and reacting the immune cell 10 with the second antibody 124 (S130); introducing a first auxiliary antibody 137, containing an auxiliary phosphor 138, into the first mixed solution, in which the nanowire complex 100 and the immune cell solution are mixed, to produce a second mixed solution and to sandwich-bind an immunological substance 138, the first antibody 134, and the first auxiliary antibody 137 released by the immune cell 10 (S150); and irradiating excitation light to the second mixed solution in such a manner that the phosphor 126 emits light and light emission of the auxiliary phosphor 138 by the emission of the phosphor is detected (S170).

The nanowire complex 100 is prepared (S110). The preparation of the nanowire complex 100 is performed as described above.

Peripheral blood mononuclear cells (PBMCs) isolated from human blood includes a specific immune cell to which an antibody for capturing an immune cell binds, and the specific immune cell may be isolated. That is, the immune cell solution may be isolated from the blood to include specific immune cell (peripheral blood mononuclear cell) through centrifugation. A peripheral blood mononuclear cell is isolated from peripheral blood using Ficoll-Hypaque density gradient centrifugation. An immune cell solution containing a peripheral blood mononuclear cell is prepared (S120).

The immune cell may be a CD8-positive (CD8+) T cell. A nanowire complex 100, in which a second antibody (antibody for capturing an immune cell) binds to a CD8 molecule for capturing CD8+ T cells, is mixed with an immune cell solution (peripheral blood mononuclear cell solution) to produce the first mixed solution, and the produced first mixed solution reacts at 4 degrees Celsius for an hour (S130).

Moreover, to confirm capturing efficiency and specificity of the antibody for immune cell of the nanowire complex 100 binding to a CD8+ T cell, the CD8+ T cell and an antibody for a distinguishable fluorescently labeled CD3 molecule may be mixed to react to each other during a reaction.

After the lapse of a predetermined time, the nanowire complex 100 unreacted to the CD8+ T cell may be removed. The removal of the unreacted nanowire complex 100 may be performed using a centrifuge (S140). After the unreacted nanowire complex 100 is removed by a centrifuge, a reacted nanowire complex 100 may be washed twice using a phosphate buffered solution (PBS).

The first auxiliary antibody 137 containing the auxiliary phosphor 138 is introduced into the first mixed solution, in which the nanowire complex 100 and the immune cell solution are mixed, to produce a second mixed solution. Accordingly, the immunological substance 138, the first antibody 134, and the first auxiliary antibody 137 released by the immune cell 10 bind in a sandwich manner (S150). The first auxiliary antibody 137 is the same as the first antibody 134 but may not include the auxiliary phosphor 138. The first auxiliary antibody 137 may be an auxiliary antibody for IFN-γ detection, and auxiliary antibody for IFN-γ detection may include an auxiliary phosphor 138 reacting to another epitope (antibody recognition site). The auxiliary phosphor 138 may be an Alexa Fluor 488 (trademark) phosphor. The first antibody, the auxiliary antibody, and the immunological substance perform sandwich binding.

The first auxiliary antibody 137, which does not sandwich-bind to the first antibody 134, may be removed (S160). Specifically, removal of the first auxiliary antibody 137, which does not sandwich-bind to the first antibody 134, may be performed using a centrifuge. After the first auxiliary antibody 137, which does not sandwich-bind to the first antibody 134, is removed by the centrifuge, the reacted nanowire complex 100 may be washed using the PBS.

Excitation light is irradiated to the second mixed solution in such a manner that the phosphor 126 emits light and light emission of the auxiliary phosphor 138 by the emission of the phosphor is detected (S170). The excitation light is in an ultraviolet region, and an emission spectrum formed by the phosphor 126 may have a maximum at 420 nm. An emission spectrum formed by the auxiliary phosphor 138 may have a maximum at 500 nm.

A confocal laser scanning microscope (CLSM) and photoluminescence (PL) apparatus detect and analyze fluorescence of the auxiliary phosphor.

Analysis of Capturing Efficiency of Immune Cell

A peripheral blood mononuclear cell is isolated from peripheral blood using Ficoll-Hypaque density gradient centrifugation. Capturing efficiency of a specific immune cell, to which the antibody for capturing an immune cell (the second antibody) of the nanowire complex 100 binds, is analyzed by a flow cytometry. To this end, the nanowire complex 100, in which the second antibody (the antibody for capturing an immune cell) binds to CD8+ T-cells, is mixed with peripheral blood mononuclear cells and react at 4° C. for an hour.

Moreover, to confirm capturing efficiency and specificity of the antibody for immune cell of the nanowire complex 100 binding to a CD8+ T cell, the CD8+ T cell and an antibody for a distinguishable fluorescently labeled CD3 molecule may be mixed to react to each other during the reaction.

After an hour, the nanowire complex 100 unreacted to the CD8+ T cell is washed twice using the PBS to be removed, and the capturing efficiency of the antibody for capturing an immune cell binding to the nanowire complex 100 is measured by a flow cytometry.

Figure 5:
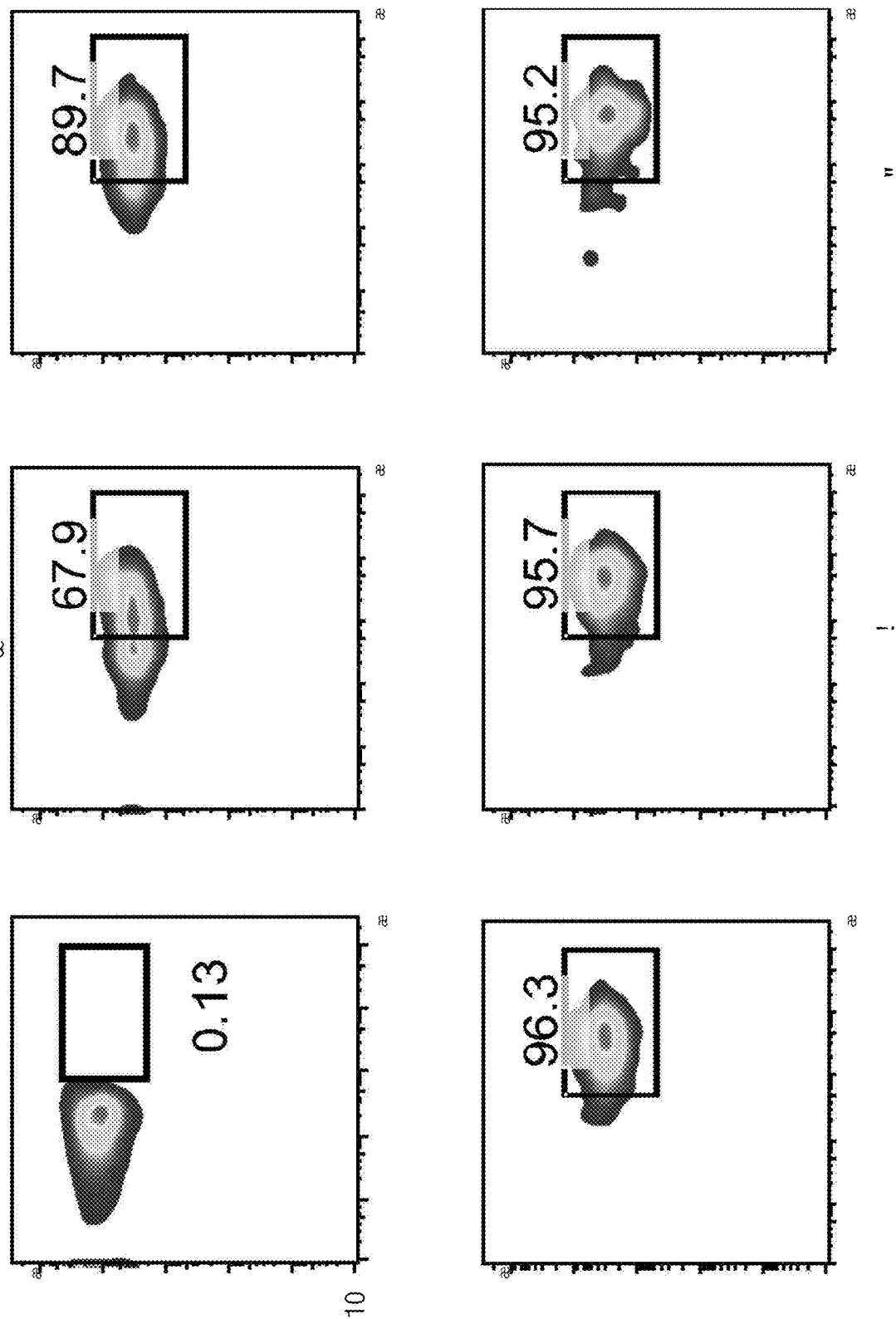
FIG. 5 is graphs illustrating capturing efficiency of an antibody for capturing an immune cell measured by a flow cytometry.

FIG. 5 is graphs illustrating capturing efficiency of an antibody for capturing an immune cell measured by a flow cytometry.

Referring to FIG. 5, X-axis represents fluorescence intensity of the phosphor (BV421) attached to a nanowire complex 100. That is, the X-axis is proportional to the amount of the nanowire complex 100. Y-axis represents the fluorescence intensity of a dye (fluorescently labeled CD3 molecule) of a dyed CD8+ T cell. That is, the Y-axis is proportional to the number of CD8+ T cells. As the amount of nanowire complexes 100 increases, results shift to a square box in which both a phosphor (BV421) and a fluorescence attached to the CD8+ T cell are visible. Accordingly, CD8+ T cells are being captured. In FIG. 5, 1 AU refers to an arbitrary concentration of a nanowire. An actual measured value is about 2.75 μg/mL per 1 AU, and only a significantly small amount of nanowire was used as compared to a conventional nanomaterial-based biosensor.

A CD3 antibody may capture CD3 and CD4 T cells. A concentration of the nanowire complex was measured at 0, 5 AU, 10 AU, 20 AU, 40 AU, and 80 AU. In this case, the square box represents cell capturing efficiency of the nanowire complex.

As the amount of the nanowire, to which an antibody for capturing an immune cell for CD8 molecules binds, increases from 5 AU to 80 AU, the fluorescence intensity of a phosphor (BV421) increases. Thus, the capturing efficiency of the CD8+ T cell increased from 0.13 to 95.2%, which was confirmed to verify cell capturing performance of the nanowire complex.

Analysis of Detection Sensitivity Through Biomolecular Quantitative Analysis

In the nanoparticle complex 100, interferon-γ (IFN-γ) was quantitatively analyzed to measure detection sensitivity of an immunological substance. The amount of the IFN-γ, which an immunological substance, was adjusted after the amount of the nanowire complex 100 was fixed to 687.5 nanogram (ng). Then, the IFN-γ was mixed with a nanowire complex solution to induce an antigen-antibody reaction at room temperature for two hours. A first antibody (an antibody for detecting IFN-γ) of the nanowire complex 100 reacts to the IFN-γ which is an immunological substance.

Remaining unreacted immunological substances (IFN-γ) are washed using a phosphate buffered solution (PBS) to be removed.

An antibody for detecting IFN-γ, attached to the nanowire complex 100, and an auxiliary antibody for detecting IFN-γ, having an AF488 phosphor reacting to another epitope (an antibody recognition site), sandwich-bind with IFN-γ interposed therebetween.

After reacting at room temperature for two hours, an antibody for detecting the remaining unreacted IFN-γ is washed using the phosphate buffered solution (PBS) to remove residues.

A nanowire complex solution, in which a final reaction is completed, is fully dispersed to 200 μL. Quantitative analysis of the detected immunological substance is performed by comparing intensities of a relative fluorescence unit of a multi-detection microplate reader. In this case, a fluorescent detection wavelength band of the auxiliary phosphor (AF488 phosphor) is 535 nm.

Figure 6:
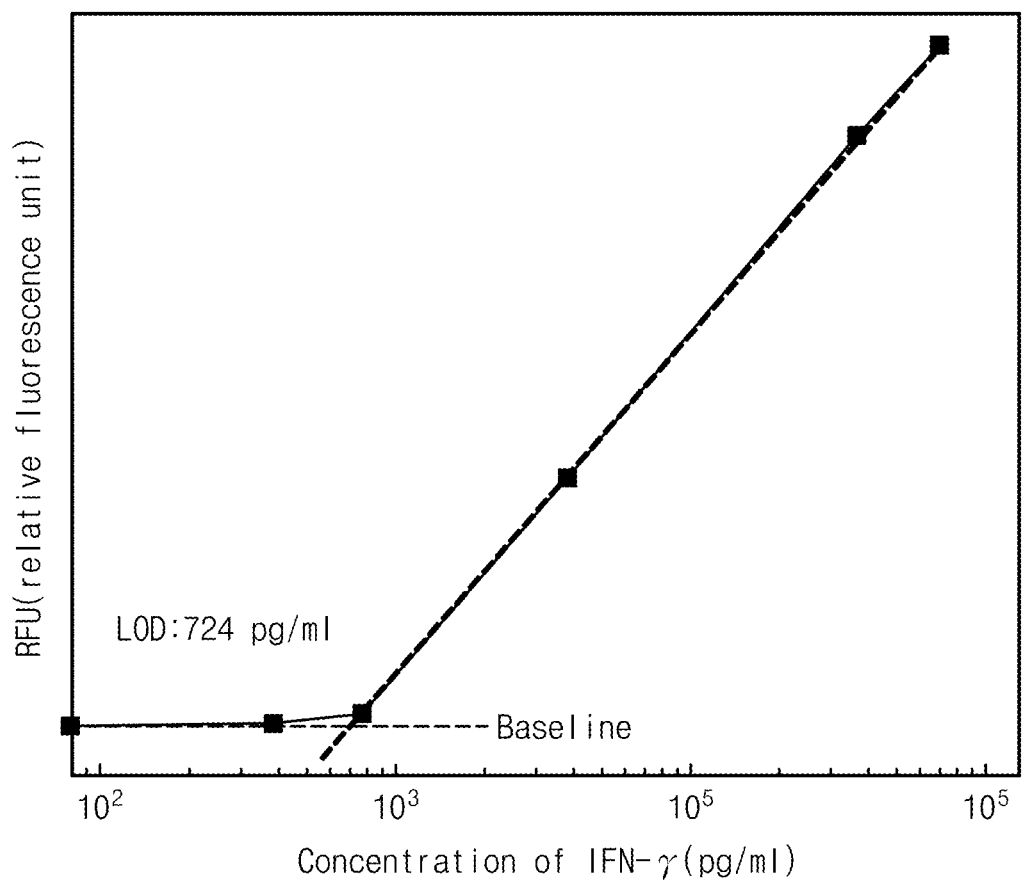
FIG. 6 is a graph illustrating an intensity of a relative shape depending on a concentration of an immunological substance (IFN-γ) of a nanowire complex according to an example embodiment of the present disclosure.

FIG. 6 is a graph illustrating an intensity of a relative shape depending on a concentration of an immunological substance (IFN-γ) of a nanowire complex according to an example embodiment of the present disclosure.

Referring to FIG. 6, a limit of detection (LOD) of IFN-γ is 724 in spite of a concentration (13.75 μg/mL) of a significantly small amount (5 AU) of nanoparticle complex 100. Such a detection limit is lower than a detection limit of a commercial immunodetector.

Figure 7:
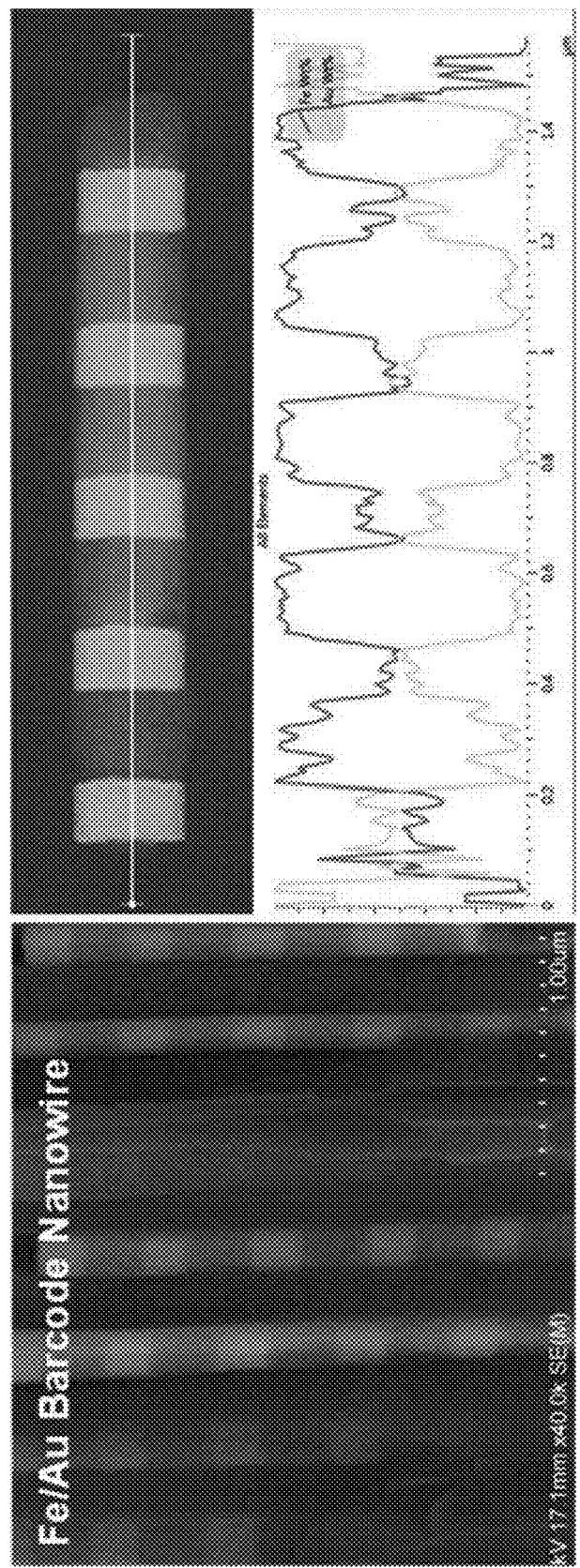
FIG. 7 are a high-resolution transmission electron microscopy (HRTEM) image and an energy dispersive spectrometry (EDS) image of an iron/gold multilayer nanowire manufactured by an electroplating method for the present disclosure.

FIG. 7 are a high-resolution transmission electron microscopy (HRTEM) image and an energy dispersive spectrometry (EDS) image of an iron/gold multilayer nanowire manufactured by an electroplating method for the present disclosure.

Referring to FIG. 7, a multilayer nanowire includes 20 nm iron layer and 20 nm gold layer which are alternately stacked. Referring to EDS data, weight percentage of iron and weight percentage of gold have a constant period. Accordingly, a structure of an iron/gold multilayer nanowire is confirmed.

Figure 8A:
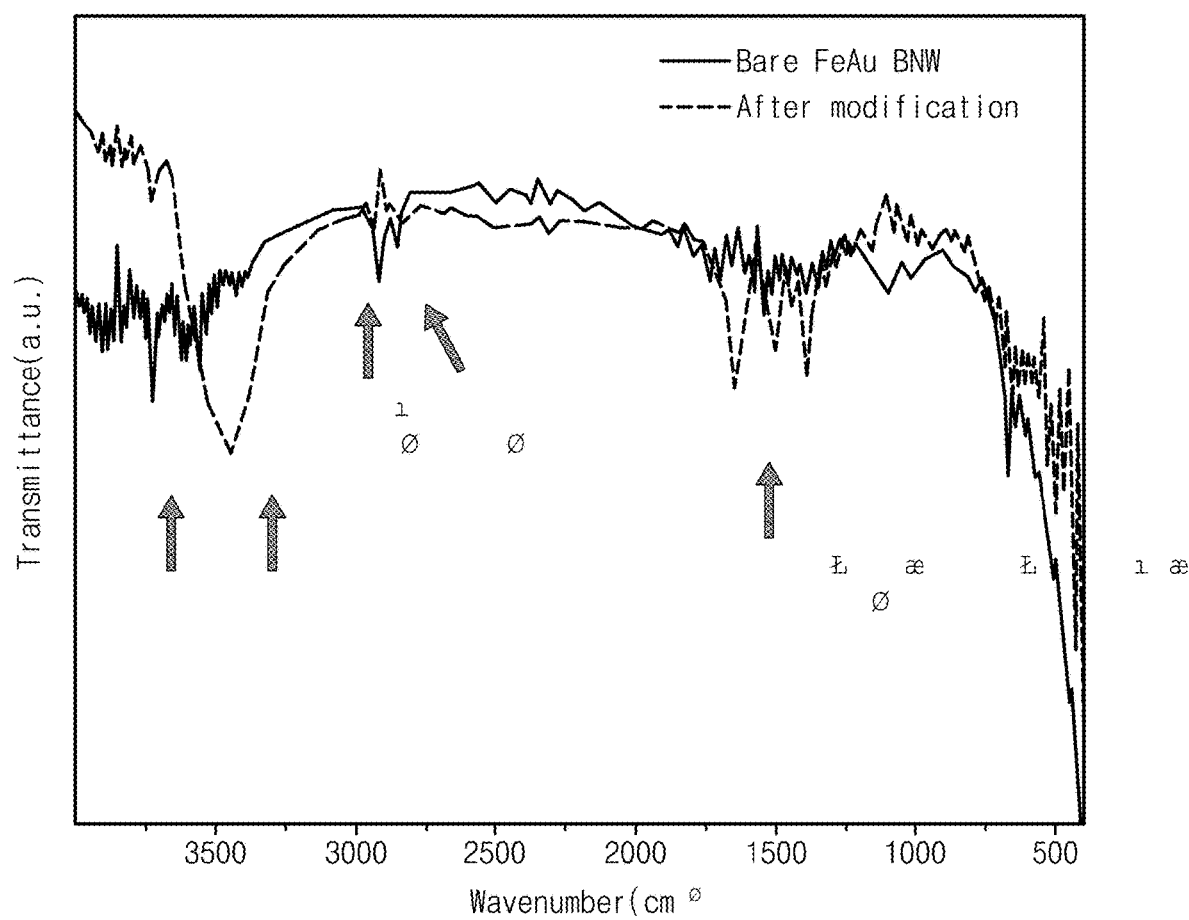
FIGS. 8A and 8B illustrates results indicating a Fourier transform infrared spectrum (FTIR) and a zeta potential, respectively.
Figure 8B:
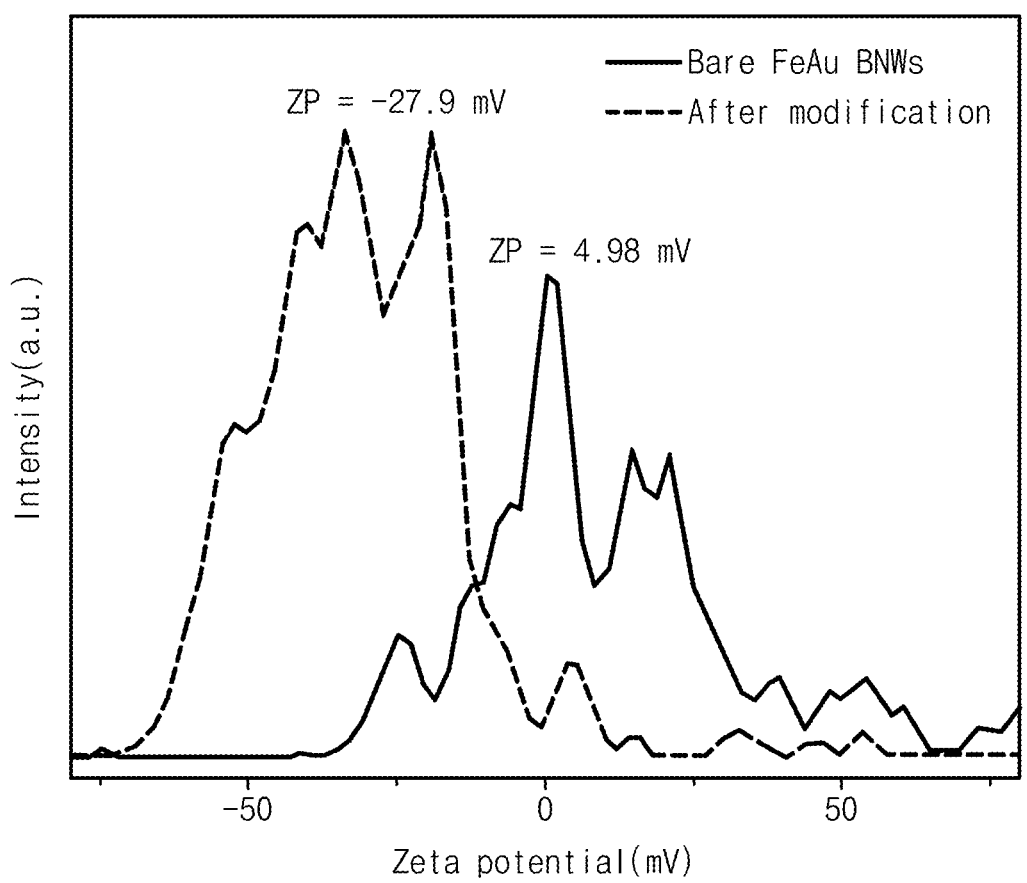

FIGS. 8A and 8B illustrates results indicating a Fourier transform infrared spectrum (FTIR) and a zeta potential, respectively.

Referring to FIGS. 8A and 8B, a surface treatment of the nanowire 110 is performed on a second metal (iron) using 11-aminoundecanoic acid having both an amine group and a carboxyl group at both ends thereof. Referring to an FTIR result, an $NH_2$ peak and a COO— peak, undetected in a nanowire before a surface treatment, are detected. From a difference before and after a surface functional group treatment, it can be seen that the nanowire 110 is a multilayer nanowire coated with the carboxyl group by binding of the amine group and the iron layer.

Figure 9A:
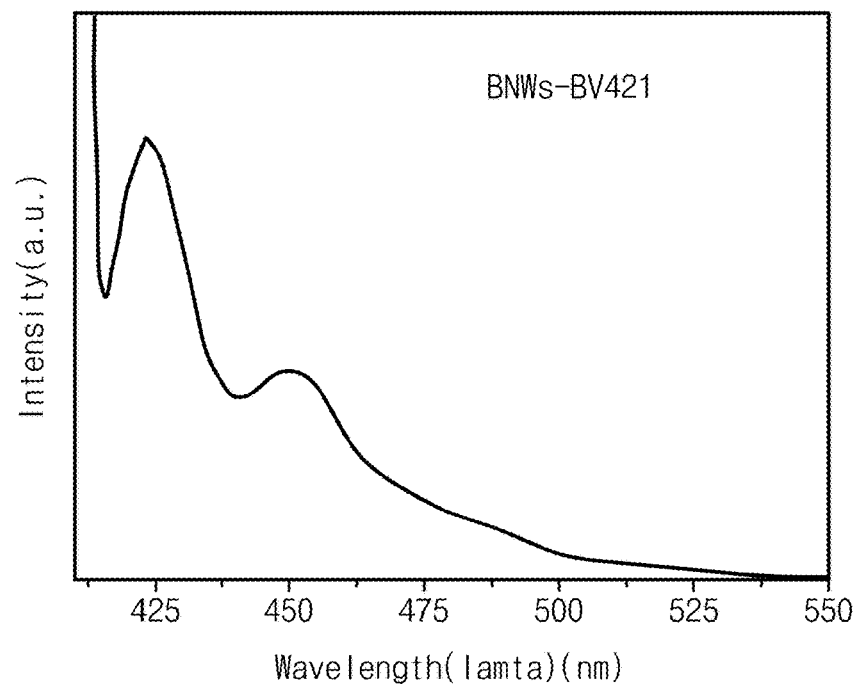
FIG. 9A illustrates a luminescence result of a barcode nanowire with which a fluorescent material (Brillant Violet™ BV421) is linked.
Figure 9B:
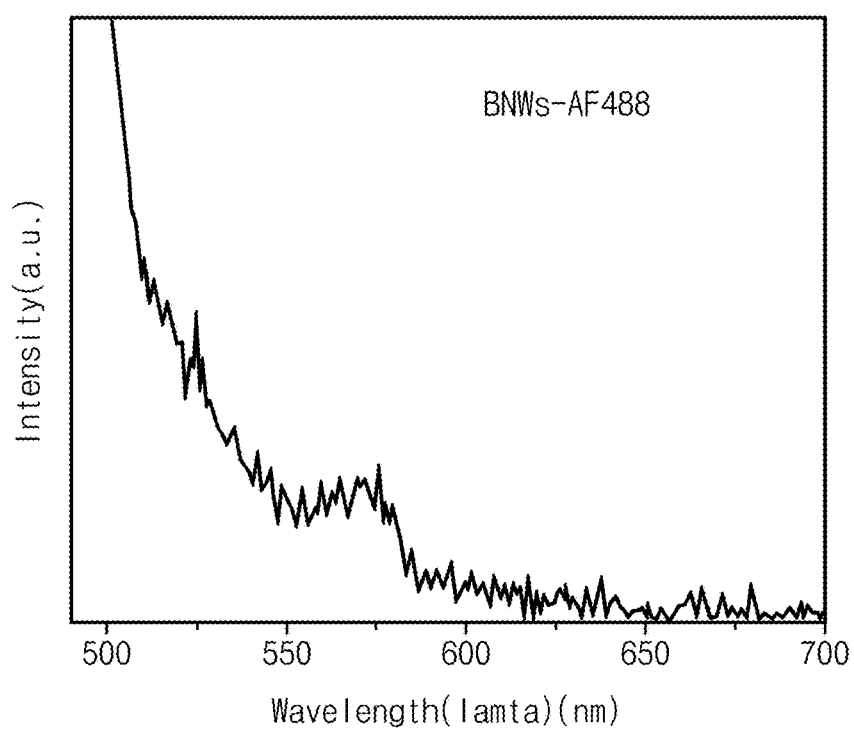
FIG. 9B illustrates a luminescence result of a barcode nanowire with which a fluorescent material (Alexa Fluor™ AF488) is linked.

FIG. 9A illustrates a luminescence result of a barcode nanowire with which a fluorescent material (Brillant Violet™ BV421) is linked FIG. 9B illustrates a luminescence result of a barcode nanowire with which a fluorescent material (Alexa Fluor™ AF488) is linked.

Referring to FIGS. 9A and 9B, a fluorescence spectrum of a phosphor (BV421) binding to a second antibody exhibits a peak at 455. In addition, a fluorescence spectrum of an auxiliary phosphor (AF488) binding to a first auxiliary antibody exhibits a peak at 500 nm. Excitation light has a wavelength of 405 nm.

Figure 10:
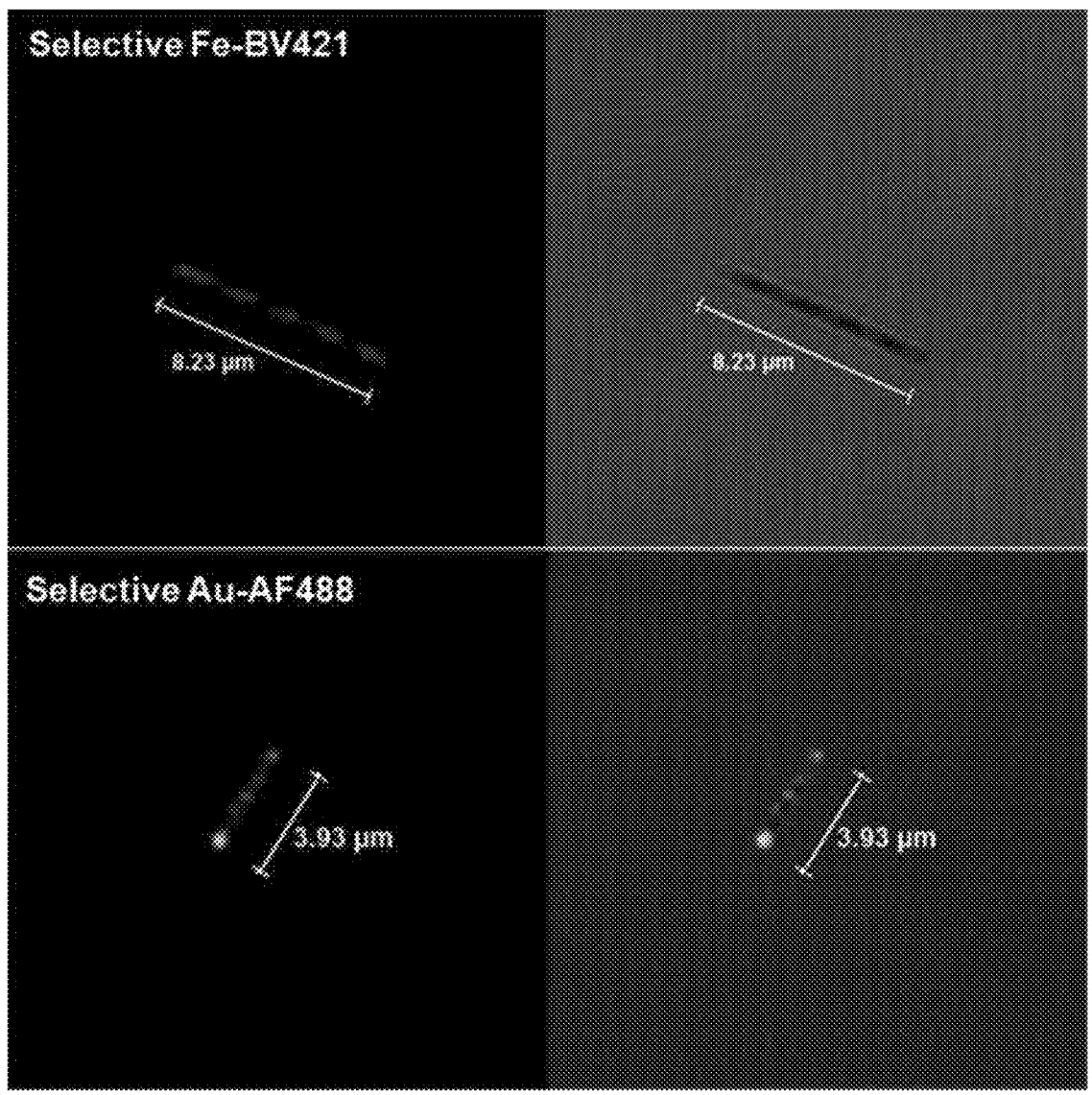
FIG. 10 is confocal laser scanning microscope images illustrating a nanowire complex.

FIG. 10 is confocal laser scanning microscope images illustrating a nanowire complex.

Referring to an upper image of FIG. 10, a phosphor (BV421) binding to a second antibody exhibits fluorescence only in a second metal (iron) of a nanocomplex. That is, an antibody for capturing a cell (the second antibody) for immune cells (CD8+ T cells), to which the phosphor (BV421) binds, is selectively attached to the second metal (iron) only by steric hindrance and selective chemical reaction.

A lower image of FIG. 10 shows that after an antibody for detecting IFN-γ selectively fixed to a first metal (gold) of the nanocomplex binds to IFN-γ in an antigen-antibody binding manner, an auxiliary antibody for detecting IFN-γ, to which an Alexa Fluor™ 488 (AF488) phosphor binds, forms sandwich binding.

FIG. 11 illustrates a result obtained by confirming an increase in fluorescent intensity of a donor after bleaching fluorescence of an acceptor to check fluorescent resonance energy transfer (FRET) occurring between a phosphor and an auxiliary phosphor.

Referring to FIG. 11, FRET efficiency is 14.4 percent.

A multilayer nanowire complex according to an example embodiment of the present disclosure includes a biocompatible material and may be stably biofunctionalized by an organic molecule, including a functional group, and an antibody. An antibody for detecting a biomolecule and an antibody for capturing a cell are loaded on the multilayer nanowire complex. The antibody for capturing a cell includes a phosphor, and the antibody for detecting a biomolecule binds to an antibody for detecting a biomolecule with an immunological substance sandwiching therebetween. The antibody for capturing a cell of the multilayer nanowire complex may capture target cells including immune cells. In addition, a specific immune cell, to which an antibody for capturing a cell binds, releases immunological substances by stimulation of an antigen or the like (for example, antigenic stimulation). Accordingly, the antibody for detecting a biomolecule of the multilayer nanowire complex sandwich-binds to the released immunological substance and an externally introduced auxiliary antibody for detecting a biomolecule. Externally provided excitation light emits a phosphor in a first wavelength band, and the emission of the phosphor causes the auxiliary phosphors, attached to the auxiliary antibody for detecting a biomolecule, to be emitted in a second wavelength band by fluorescence resonance energy transfer (FRET). Accordingly, when the emission intensity of the second wavelength band is detected, the concentration of an immunological substance may be detected with high sensitivity. As a result, the multilayer nanowire complex may be applied to various biomedical fields such as disease diagnosis, immunotherapy, and the like.

The multilayer nanowire complex according to an example embodiment of the present disclosure may diagnose an immunological substance through various apparatuses capable of measuring fluorescence rather than a high-priced flow cytometry analyzer.

In particular, the present disclosure proposes an immunological test technique, superior to a related-art method of Langmuir Vol 22, pp 105828-10534 (2006), ACS Nano Vol 7, pp 9771-9779 (2013), which may selectively and simultaneously heterogeneous antibodies and may have high accuracy and efficiency using fluorescent resonance energy transfer (FRET).

Although the present disclosure and its advantages have been described in detail, it should be understood that various changes, substitutions and alterations can be made herein without departing from the spirit and scope of the disclosure as defined by the following claims.

What is claimed is:

1. An immunological substance detection nanowire complex comprising:
    a multilayer nanowire in which a first metal and a second metal are alternately stacked;
    a polymer comprising an amine group at a first end and a carboxyl group at a second end, and attached to the second metal through the amine group;
    a first antibody attached to the first metal through a thiol group; and
    a second antibody comprising a first phosphor and attached to the carboxyl group of the polymer,
    wherein the first antibody sandwich-binds to an immunological substance and a third antibody comprising a second phosphor,
    wherein when the second antibody binds to an immune cell, the first phosphor of the second antibody receives an external light to emit a first fluorescence having a first wavelength, and the second phosphor of the third antibody receives the first fluorescence to emit a second fluorescence having a second wavelength by a fluorescent resonance energy transfer (FRET), and
    wherein an average distance between the first phosphor and the second phosphor is within 10 nm.

2. The immunological substance detection nanowire complex of claim 1, wherein the first metal is gold (Au), and the second metal is a ferromagnetic material including at least one of iron (Fe), nickel (Ni), and cobalt (Co).

3. The immunological substance detection nanowire complex of claim 1, wherein a polymer, having both a carboxyl group and an amine group at both ends thereof, is connected with an ethyl group or polyethylene glycol.

4. The immunological substance detection nanowire complex of claim 1, wherein a polymer, having both a carboxyl group and an amine group at both ends thereof, is 11-aminoundecanoic acid.

5. The immunological substance detection nanowire complex of claim 1, wherein the first metal of the multilayer nanowire has a thickness of 20 nanometers (nm) to 50 nm, and the second metal of the multilayer nanowire has a thickness of 20 nm to 50 nm.

6. The immunological substance detection nanowire complex of claim 1, wherein the immune cell is a CD8+ T cell, and the immunological substance is interferon-gamma (IFN-γ).

* * * * *